United States Patent [19]

Vanlerberghe et al.

[11] 4,294,728

[45] Oct. 13, 1981

[54] SHAMPOO AND/OR BUBBLE BATH COMPOSITION CONTAINING SURFACTANT AND 1,2 ALKANE DIOL

[75] Inventors: Guy Vanlerberghe, Montjay-La-Tour; Henri Sebag, Paris; Claire Fiquet, Paris, all of France

[73] Assignee: Société Anonyme dite: L'Oreal, Paris, France

[21] Appl. No.: 97,492

[22] Filed: Nov. 26, 1979

Related U.S. Application Data

[63] Continuation of Ser. No. 565,130, Apr. 4, 1975, abandoned, which is a continuation of Ser. No. 227,299, Feb. 17, 1972, abandoned.

[30] Foreign Application Priority Data

Feb. 17, 1971 [LU] Luxembourg ............................ 62616
Feb. 17, 1971 [LU] Luxembourg ............................ 62617

[51] Int. Cl.$^3$ ........................ C11D 1/835; A61K 7/06

[52] U.S. Cl. .................................... 252/542; 252/546; 252/547; 252/548; 252/545; 424/70

[58] Field of Search ............... 252/541, 545, 548, 547, 252/546, 542; 424/70, 358

[56] References Cited

U.S. PATENT DOCUMENTS

| | | | |
|---|---|---|---|
| 2,927,901 | 3/1960 | Charret | 252/153 |
| 2,956,025 | 10/1960 | Lew | 252/559 |
| 3,072,580 | 1/1963 | Laiderman | 252/545 X |
| 3,156,656 | 10/1964 | Libby | 252/153 |
| 3,328,307 | 6/1967 | Schmitz | 252/106 |
| 3,341,460 | 9/1967 | Wei | 252/153 X |
| 3,449,430 | 6/1969 | Dohr et al. | 260/583 |
| 3,533,955 | 10/1970 | Pader et al. | 252/153 |
| 3,708,364 | 1/1973 | Kalopissis et al. | 252/156 |

*Primary Examiner*—P. E. Willis, Jr.
*Attorney, Agent, or Firm*—Cushman, Darby & Cushman

[57] ABSTRACT

A shampoo or bubble bath composition contains in combination a cationic, amphoteric or zwitterionic surfactant and at least one 1,2-alkane diol. Preferably, the composition also includes a nonionic surfactant.

8 Claims, No Drawings

SHAMPOO AND/OR BUBBLE BATH COMPOSITION CONTAINING SURFACTANT AND 1,2 ALKANE DIOL

This application is a continuation of our application Ser. No. 565,130, filed Apr. 4, 1975, now abandoned which, in turn, is a continuation of our application Ser. No. 227,299, filed Feb. 17, 1972, now abandoned.

The present application relates to a new foamable composition, especially a cosmetic composition, and more particularly, a shampoo and bubble bath composition comprising in combination a surfactant and one or more dihydric alcohols to improve the foaming characteristics of said surfactant.

The surfactant that can be used in the present invention has at least one nitrogen atom joined directly or indirectly to the fatty chain, said nitrogen atom being positively charged or capable of being positively charged by addition of a mineral or organic acid or by quaternization according to known processes, or it has a positively charged sulfur atom or it has both said nitrogen atom and said positively charged sulfur atom. Filling this definition are cationic surfactant compounds such as amines, amine oxides, their salts, their quaternaries and sulfoniums, as well as amphoteric and zwitterion surfactant compounds.

The presence of the dihydric alcohol improves not only the foaming properties but also the detergent properties of the above-mentioned surfactants, and it also facilitates untangling of washed hair, either wet or after drying.

These dihydric alcohols are neither water soluble nor foaming, and the improvement effected in the above-mentioned compositions is thus often due to a synergistic effect.

BACKGROUND OF THE INVENTION

Heretofore it has been known to utilize alcohols with surfactants.

Representative of such technology are the following patents:

British Pat. No. 854,994 describes a shampoo containing a cationic surface active agent together with either an ampholytic or a nonionic surface active agent in combination with a hair conditioner which can be a fatty alcohol containing 12–30 carbon atoms. Specifically the patent teaches the use of cetyl alcohol, stearyl alcohol, arachidyl alcohol, behenyl alcohol, ricinoleyl alcohol, monocetylether of glycerol, glyceryl monostearate, ethylene glycol monopalmitate, diethylene glycol monostearate, monostearyl ether of ethylene glycol and stearic monoethanolamide.

British Pat. No. 843,379 describes a shampoo composition containing as a surface active agent the sodium salt of N-acyl N-methyl taurine, optionally mixed with the sodium, magnesium or triethanol amine salt of alkylsulfuric acid. In this composition there can be used, as a solubilizing agent, an alkylolamide of a fatty acid. There can also be present a branched chain aliphatic dialcohol. There is also suggested the use of a fatty alcohol containing 10–14 carbon atoms to improve the quantity and stability of the foam. However, the surface active agent employed therein is not that defined in the present invention.

U.S. Pat. No. 3,449,430 describes a shampoo composition using an amino oxide type surface active agent. There is also included in the disclosed composition, as super-fatting agents, fatty acids, fatty alcohols, fatty esters and lanolin.

U.S. Pat. No. 2,879,231 describes a sprayable aerosol shampoo composition containing, as the detergent, the ammonium salts of sulfated monoglyceride of higher fatty acids, as well as a saturated higher fatty alcohol having 12–16 carbon atoms to improve not only the foam but also the hydroalcoholic solvent characteristics thereof.

Netherlands Pat. No. 73,501 describes the use of 1,2-alkane diols having at least 9 carbon atoms to improve the foam stability of anionic detergents having the formula RX, wherein R is a hydrocarbon radical having more than 7 carbon atoms and X is a sulfuric, sulfonic or carboxylic residue or an acid residue containing an atom of phosphorus. However, this patent does not teach or suggest the use of these 1,2-alkane diols in combination with the surfactants of the present invention.

French Pat. No. 1,489,243 discloses a liquid detergent composition and, in particular, a shampoo composition comprising an aqueous layer and a liquid layer not miscible with water. By agitating these layers a temporary oil-in-water emulsion is created. The composition includes a foam improver and an emulsion destabilizer, the latter being used to insure the temporary nature of the emulsion created by agitating or mixing the respective layers together. As an emulsion destabilizer, there is recommended an aliphatic monoalcohol containing 1–7 carbon atoms or an aliphatic dialcohol containing 2–7 carbon atoms, such as ethylene glycol, propylene glycol or hexylene glycol.

German Pat. No. 700,677 describes the use of dialcohols as anti-foam agents with gelatin, casein and blood albumin.

DETAILED DESCRIPTION OF THE INVENTION

The present invention relates to a shampoo composition or a bubble bath composition comprising an aqueous solution of at least one cationic, amphoteric or zwitterionic surfactant and at least one dihydric alcohol. In a preferred embodiment, the shampoo composition or bubble bath composition also includes a nonionic surfactant.

Representative cationic surfactants that can be used in the compositions of the present invention include:

(1) compounds constituted essentially by a fatty chain joined directly or indirectly to a nitrogen atom which can be present in the molecule in the form of a free base, when such a molecule is water soluble, or an amine oxide, or a mineral or organic acid salt thereof, or a corresponding quaternization compound prepared by conventional methods; and (2) sulfonium type compounds.

Compounds (1) can be an amine, an amine oxide, or a quaternary ammonium compound. They can also contain a sulfonium functional group. Representative amine type compounds include (a) compounds whose lipophilic chain may be joined directly to the nitrogen atom as in formula (1)

wherein R is alkyl, alkylaryl or a mixture thereof, having a total of 10–24 carbon atoms derived from natural fatty acids of animal or vegetable origin, or from fatty acids of synthetic origin; and alkenyl having 10 to 24 carbon atoms; the said alkyl and alkenyl moieties being straight or branched; and $R_1$ and $R_2$ each independently represent a monovalent radical selected from the group consisting of hydrogen, methyl, ethyl, phenyl, hydroxyethyl, polyethoxy hydroxyethyl, hydroxypropyl and dihydroxypropyl; or $R_1$ and $R_2$ together form with the nitrogen atom to which they are attached a heterocycle which can include an oxygen atom or another nitrogen atom, thus forming a heterocyclic amine selected from the group consisting of pyrrolidine, morpholine and piperidine;

(b) compounds whose lipophilic chain is joined to the terminal nitrogen by a chain of atoms that can comprise, in addition to carbon and hydrogen atoms, one or more atoms such as nitrogen, oxygen or sulfur.

These compounds can be prepared for example:

(i) by condensation of polyamines on alkyl halides, or by cyanoethylation of the fatty amines followed by catalytic hydrogenation;

(ii) by cyanoethylation of fatty alcohols, or by condensation of secondary amines on fatty chain epoxides or on corresponding halohydrins. Thus, for example, according to the invention use can be made of compounds of the formula:

$$R-O-[C_2H_3O(CH_2OH)]_n-CH_2-CHOH-N\begin{matrix}R_1\\R_2\end{matrix}$$

wherein R, $R_1$ and $R_2$ have the same meaning given above, n designating an average statistical value of 0.5 to 10, and $-[C_2H_3O(CH_2OH)]-$ representing one of the two isomers

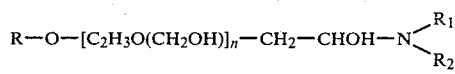

These compounds can be prepared according to French Pat. No. 1,538,525;

(iii) by condensation of mercaptans on secondary amines in the presence of formaldehyde, or by condensation of mercaptans on tertiary amines which have an epoxide function, or from secondary amines with halohydrins that have a thioether function;

(iv) by condensation of a fatty acid or the chloride thereof on a dialkylaminoethanol or on hydroxyethylene dialkylaminoethanol, or by condensation of a secondary amine and epichlorohydrin on a sodium or potassium soap in accordance with the French Pat. No. 1,313,143; and (v) by condensation of a fatty acid or the corresponding chloride or ester thereof, on a primary-tertiary amine such as dimethyl or diethylaminoethyl or propyl amine, or on a secondary-tertiary amine; and (c) compounds of the alkyl imidazoline type having the formula

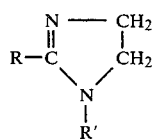 (3)

wherein R has the same meaning given above and R' is selected from the group consisting of hydrogen, —CH$_2$—CH$_2$OH,

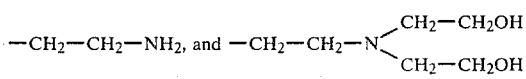

Representative compounds of the amine oxide type include those that are obtained from the above described tertiary bases, by conventional processes, e.g. by oxidation with hydrogen peroxide, possibly in the presence of a lower organic acid, such as acetic acid.

In the case of compounds with an intermediate thioether function, with sufficient quantities of hydrogen peroxide there are formed amine oxides with a sulfoxide or sulfone function.

The above amino compounds are used in the form of salts of mineral acids such as hydrobromic, hydrochloric, sulfuric, phosphoric acid or salts of organic acids such as acetic, lactic, citric, tartaric, para-toluene sulfonic or salicylic acid, or in the form of free bases when the compounds are water soluble.

Representative compounds of the quaternary ammonium type include those that can be obtained by quaternizing aliphatic tertiary amines or aliphatic aryl amines, more especially fatty dimethylamines, by known processes, i.e. for example using compounds such as methyl iodide, methyl bromide, methyl chloride, ethyl chloride, bromide or iodide, benzyl chloride or bromide, dimethyl sulfate, an alkyl mesylate or tosylate, chloracetamide, glycol or glycerol chlorohydrin, ethylene oxide, propylene oxide and glycidol. They can also be prepared by quaternizing aromatic or heterocyclic amines such as pyridine, 2-, 3- and 4-picolines, quinoline, and the N-alkyl morpholines, etc. with fatty chain alkyl halides, preferably with alkyl bromides or alkyl mesylates or tosylates. Additionally, they can also be prepared by o-alkylation of amine oxides using agents such as ethyl or methyl iodide, bromide or chloride, dimethyl sulfate or alkyl mesylates or tosylates. In the case of tertiary amines or amine oxides with a thioether function, quaternary sulfoniums are obtained.

Representative sulfonium type compounds include those that can be obtained from corresponding thioethers by processes similar to the quaternizing processes mentioned above.

Representative amphoteric and zwitterion compounds of the betaine type include those that can be readily prepared by known processes such, for example, as by condensation of halogen alkane carboxylic acids and, essentially, chloro or bromo acetic or propionic acid on primary, secondary or tertiary fatty amines, or by action of halogenated diacids, such as chlorosuccinic acid, on the same amines. Additionally, they can be prepared by condensation of amino acids on alkyl halides, on chloromethyl ethers derived from higher alcohols, or on fatty chain epoxides. They can also be prepared by condensation of primary, secondary or tertiary amines, including heterocyclic amines, such as pyridine, on fatty α-halogenated acids or by addition of primary or secondary fatty amines on acid compounds with an activated double bond such as, for example, acrylic acid or acids derived from maleamic acid, according to the method described in French Pat. No. 1,344,212. Moreover, these compounds can be prepared by condensation of halogen alkane carboxylic acids such as chloracetic acid on alkyl thioethers, e.g. dodecyl and methyl sulfide. It is possible to obtain a non-nitrated ampholytic compound of the carboxylic sulfonium type which can also be used within the scope of the invention.

The dihydric alcohols that can be utilized in the present invention are saturated compounds having a straight chain containing from 10 to 18, preferably 10 to 14, odd or even, carbon atoms, of which the two hydroxyl groups are in the 1 and 2 positions. These dihydric alcohols can be obtained conveniently by hydroxylation of α-olefins or by hydrolysis of corresponding epoxides.

Representative dihydric alcohols include 1,2-decane diol, 1,2-dodecane diol, 1,2-tetradecane diol or a mixture thereof, or also a mixture of alkane diols, such as mixtures of 1,2-undecane diol, 1,2-dodecane diol, 1,2-tridecane diol, 1,2-tetradecane diol, and also 1,2-pentadecane diol, 1,2-hexadecane diol, 1,2-heptadecane diol and 1,2-octadecane diol.

Preferably the compositions of the present invention utilize 1,2-decane diol, 1,2-dodecane diol, 1,2-tetradecane diol and mixtures thereof.

These α-diols, which can play a synergistic role in the present invention, are non-foaming compounds that are insoluble in water, and are utilized in proportions of 1 to 80%, preferably from 5 to 30% by weight, based on the weight of the surfactant compounds.

As indicated above, a preferred composition in accordance with the present invention is one which also includes a nonionic surfactant.

Representative nonionic surfactants include the following:

(i) condensation products of ethylene oxide with fatty alcohols, with long chain mercaptans having, for example, 10-14 carbon atoms, or with alkyl-phenols such as octyl phenol, nonyl phenol and dodecylphenol;

(ii) compounds having the formula RO—[C$_2$H$_3$O(CH$_2$OH)]$_n$—H wherein R represents alkyl or alkenyl, straight or branched chain, having 8-22 carbon atoms, or alkylaryl having 8-22 carbon atoms wherein the alkyl moiety, linear or branched, has 2-16 carbon atoms, or R represents a hydrocarbon radical derived from alcohols obtained by the hydrogenation of lanolin or derived from natural waxes such as bees wax, resin acids or cyclic fatty acids; and in which n, representing a statistical average value, can be a whole or decimal number equal to or lower than 10;

(iii) compounds having the formula

RO—[C$_2$H$_3$O(CH$_2$OCH$_2$—CHOH—CH$_2$OH)-]$_n$—H wherein R represents alkyl or alkenyl, straight or branched chain, having 8-22 carbon atoms, carrying optionally, hydroxy radicals and some intermediate groups in which figure some heteroatoms and n, representing a statistical average value, is a number, whole or decimal, equal to or lower than 5;

(iv) compounds having the formula $$R-CH-CH_2-O-[C_2H_3O(X)]_p-H$$
$$\phantom{R-CH-CH_2}|$$
$$\phantom{R-CH-CH_2}O\phantom{-CH_2}-[C_2H_3O(X)]_q-H$$

wherein R represents a straight or branched chain hydrocarbon having 8-22 carbon atoms, optionally carrying hydroxy radicals or intermediate groups in which figure some heteroatoms, X represents CH$_2$OH or CH$_2$—OCH$_2$—CHOH—CH$_2$OH, and p and q represent a statistical average value which can be a whole or decimal number equal to or less than 10, with the sum (p+q) being equal to or greater than 1 and lower than or equal to 10;

(iv) compounds having the formula $$R-S-[CH_2-CHOH-CH_2-O]_n-H$$
$$\phantom{R-S}\downarrow$$
$$\phantom{R-S}O$$

wherein R represents alkyl, alkenyl or hydroxyalkyl, straight or branched chain, having 8-22 carbon atoms, cycloaliphatic or arylaliphatic having 8-22 carbon atoms, or a mixture thereof and n represents a statistical average value greater than 1 and equal to or less than 10;

(v) compounds having the formula

R—CHOH—CH$_2$—O—[CH$_2$—CHOH—CH$_2$)-]$_n$—H wherein R represents an aliphatic, cycloaliphatic or arylaliphatic radical or mixtures thereof, having 7-21 carbon atoms, the aliphatic chains being saturated or unsaturated, linear or branched and being able to carry oxygen atoms and/or sulfur and, in particular, ether, thioether and/or hydroxymethylene groups and n representing the average degree of polymerization is a number, whole or decimal, higher than 1 and equal to or lower than 10; and (vi) compounds having the formula $$RO-\left[\begin{array}{cc}CH-CHO\\|\phantom{X}|\\A\phantom{X}B\end{array}\right]-H$$

wherein R represents alkyl, straight or branched chain, having 8-30 carbon atoms, or alkylaryl having 12-40 carbon atoms, or alkyl-polyalkyleneoxy containing 14-60 carbon atoms, and 1-10 oxygen atoms, or a cycloaliphatic residue having 10-30 carbon atoms, one of the symbols A and B represents hydrogen and the other represents CH$_2$Z where Z represents alkylthio (R'S-) or alkylsulfinyl $$(R'S-),$$
$$\phantom{(R'S}\|$$
$$\phantom{(R'S}O$$

R' being alkyl or hydroxyalkyl having 1-4 carbon atoms; and n is a whole number between 1-20 inclusive.

The compositions of the present invention can also include ingredients and adjuvants customarily used in cosmetics to attain the specific appearance, color, odor, viscosity, pH or any other property that is desired. The compositions preferably contain a perfume and can also contain a dye as well as other additives.

These foaming compositions which can have a pH ranging between about 2.5–10.5 can be used for various industrial applications. A particularly interesting application concerns compositions for cosmetic uses such as a shampoo or a bubble bath formulation. Preferably the shampoo has a pH of 3–9.5 while the bubble bath has a pH of 6–8.

The shampoo composition usually contains 0.1–1% and preferably 0.2–0.6% perfume while the bubble bath contains 1-10%, and preferably 2-6% perfume, based on the total weight of the foaming composition.

The addition of the dihydric alcohol to the cationic, amphoteric or zwitterionic surfactant, or preferably to one or more of said surfactants in combination with a nonionic surfactant modifies the foaming, detergent and treating properties significantly, and also affects the appearance of the foam of the foaming compositions in question.

It is thus observed that there is:

(1) a very definite improvement in the initiation of foaming, which is more rapid with immediate foam division;

(2) pronounced increase in foaming power;

(3) an improvement in the appearance of the foam, which is somewhat thicker, more consistent, more smooth to the touch, hence more agreeable to handle; these properties probably being imparted by better water retention; and (4) the stability of the foam is likewise increased.

These properties are retained in the presence of fatty soil in the case of shampoos, for example, in which there is also an improvement in the detergent propeties of the compositions.

Further, there is also observed a greater ease in untangling of both wet and dry hair. The feel of the hair is also more agreeable and softer, but the hair is not made heavy thereby. The introduction of the above dihydric alcohol in shampoos imparts a substantial improvement in the shampoo quality both as to foam and as to detergent and treating effect.

Shampoo compositions usually contain 0.4-4.5%, preferably 0.6-4% by weight based on the total weight of the composition of a 1,2-alkane diol or a mixture thereof; and 0.5-30%, preferably 3-25%, by weight based on the total weight of the composition of a surfactant selected from the group consisting of (i) a surfactant having at least one nitrogen atom joined directly or indirectly to a fatty chain, said nitrogen atom being positively charged or capable of being positively charged by addition of a mineral or organic acid or by quaternization, (ii) a surfactant having a positively charged sulfur atom, and (iii) a surfactant having both a positively charged sulfur atom and a nitrogen atom joined directly or indirectly to a fatty chain; said nitrogen atom being positively charged or capable of being positively charged by addition of a mineral or organic acid or by quaternization.

Bubble bath compositions usually contain 1-10%, preferably 1.5-5%, by weight based on the total weight of the composition of a 1,2-alkane diol or a mixture thereof; and 10-80%, preferably 20-60% by weight based on the total weight of the composition of a surfactant selected from the group consisting of (i) a surfactant having at least one nitrogen atom joined directly or indirectly to a fatty chain, said nitrogen atom being positively charged or capable of being positively charged by addition of a mineral or organic acid or by quaternization, (ii) a surfactant having a positively charged sulfur atom, and (iii) a surfactant having both a positively charged sulfur atom and a nitrogen atom joined directly or indirectly to a fatty chain; said nitrogen atom being positively charged or capable of being positively charged by addition of a mineral or organic acid or by quaternization.

The improvement of the foam insofar as volume, stability and smooth feel are concerned can be demonstrated with a Ross and Miles apparatus which allows rapid and readily reproducible measurements of foam volume, foam stability and water retention.

The results obtained with different products that were tested without additives and in the presence of various amounts of synergistic agent expressed in percentage with reference to the weight of the dry surfactant are present in Table I, which illustrates the use of dihydric alcohols with a surfactant.

Thus, there are shown for surfactant concentrations of 0.5%, 0.2%, 0.05% the foam heights in centimeters, at time 0 (subscript 1) and at the end of five minutes (subscript 2) and water volumes in milliliters retained in the foam at time zero.

In Table I the synergistic agents used are either synthetic α-diols or mixtures of α-diols sold by ADM company (Archer Daniels Midland Co.) such as ADOL 114 (1,2 alkane diols with a chain length of $C_{11}$ to $C_{14}$) and ADOL 158 (1,2 alkane diols with a chain length of $C_{15}$ to $C_{18}$).

All measurements were effected in tap water with a hardness of 34° (French hydrotimetry) and a controlled temperature of 35° C., which corresponds to a temperature of practical use.

The pH indicated for each of the tested surfactants is that of a mother solution at 5% which is divided into two parts, one of which serves as control solution without additive, the other having the desired amount of dihydric alcohol.

The pH was adjusted in all cases either by use of lactic acid or by use of sodium hydroxide.

TABLE I $$C_{12}H_{25}-N \begin{matrix} (CH_2-CH_2O)_x-H \\ (CH_2-CH_2O)_y-H \end{matrix}$$

sold under the tradename "ETHOMEEN C.25"

$x + y = 15$ ， pH = 7.5

| | | Height of foam (cm.) | | | | | | Retention of water (ml.) | | |
|---|---|---|---|---|---|---|---|---|---|---|
| | | 5% | | 2% | | 0.5% | | | | |
| 1,2-alkanediol | % | 1 | 2 | 1 | 2 | 1 | 2 | 5% | 2% | 0.5% |
| Without 1,2-diol | 0 | 14.5 | 2 | 13 | 1 | 9 | | 20 | 20 | 10 |
| 1,2-dodecanediol | 10% | 17.5 | 14.5 | 15 | 12 | 14.5 | 11 | 30 | 20 | 20 |
| | | | | | | | pH = 4 | | | |
| Without 1,2-diol | 0 | 14.5 | 8 | 13 | 6 | 8.5 | | 30 | 20 | 10 |
| 1,2-dodecanediol | 10% | 20 | 16.5 | 16 | 13 | 14 | 11 | 50 | 30 | 30 |

TABLE I-continued

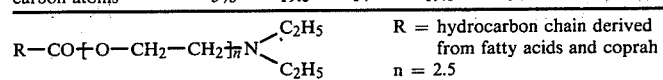
C₁₁H₂₃COO CH₂—CH₂—N(CH₂—CH₃)(CH₂—CH₃)

pH = 3.25

| | | | | | | | | | |
|---|---|---|---|---|---|---|---|---|---|
| Without 1,2-diol | 0 | 18 | 12 | 18 | 7.5 | 6 | 4.5 | 40 | 40 | 5 |
| 1,2-dodecanediol | 5% | 20.5 | 12 | 20.5 | 9 | 9.5 | 6.5 | 50 | 50 | 20 |
| 1,2-alkanediol wherein the alkane moiety has 11-14 carbon atoms | 5% | 19.5 | 14 | 19.5 | 8.5 | 7.5 | 6 | 50 | 40 | 20 |

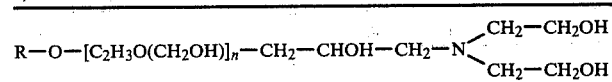
R—CO—(O—CH₂—CH₂)ₙ—N(C₂H₅)(C₂H₅)    R = hydrocarbon chain derived from fatty acids and coprah
n = 2.5 pH = 3.5

| | | | | | | | | | |
|---|---|---|---|---|---|---|---|---|---|
| Without 1,2-diol | 0 | 15 | 8 | 13 | 6 | 3 | | 40 | 30 | |
| 1,2-dodecanediol | 10% | 18 | 10 | 16 | 6 | 5.5 | 2 | 40 | 40 | 5 |

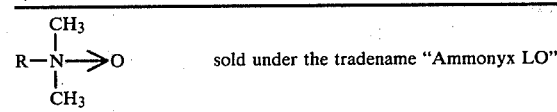
R—O—[C₂H₃O(CH₂OH)]ₙ—CH₂—CHOH—CH₂—N(CH₂—CH₂OH)(CH₂—CH₂OH)

pH = 4
n = 1

R is a hydrocarbon radical derived from oleic acid

| | | | | | | | | | |
|---|---|---|---|---|---|---|---|---|---|
| Without diol | 0 | 12.5 | 10 | 8.5 | 5 | 1.5 | | 30 | 20 | 0 |
| 1,2-dodecanediol | 10% | 15 | 11.5 | 10 | 7 | 2.5 | | 40 | 20 | 0 |

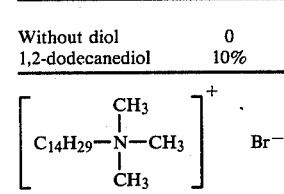
R—N(CH₃)(CH₃)→O    sold under the tradename "Ammonyx LO"

R is lauryl pH = 8.5

| | | Height of foam (cm.) | | | | | | Retention of water (ml.) | | |
|---|---|---|---|---|---|---|---|---|---|---|
| | | 5% | | 2% | | 0.5% | | | | |
| 1,2-alkanediol | % | 1 | 2 | 1 | 2 | 1 | 2 | 5% | 2% | 0.5% |
| Without diol | 0 | 17 | 4 | 16.5 | 3 | 16 | 3 | 20 | 20 | 30 |
| 1,2-dodecanediol | 10% | 20.5 | 17 | 20 | 16.5 | 18.5 | 14 | 40 | 40 | 40 | pH = 4

| | | | | | | | | | | |
|---|---|---|---|---|---|---|---|---|---|---|
| Without diol | 0 | 17 | 14 | 16 | 13.5 | 15 | 13 | 20 | 20 | 30 |
| 1,2-dodecanediol | 10% | 20 | 17 | 20 | 17 | 17.5 | 14.5 | 40 | 40 | 40 |

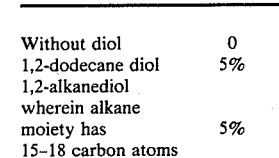
[C₁₄H₂₉—N(CH₃)(CH₃)(CH₃)]⁺ Br⁻ pH = 8

| | | | | | | | | | | |
|---|---|---|---|---|---|---|---|---|---|---|
| Without diol | 0 | 15.5 | 14 | 15.5 | 13 | 11 | 9 | 20 | 24 | 30 |
| | 3% | 20.5 | 17.5 | 18.5 | 15 | 14.5 | 12 | 40 | 40 | 40 |
| 1,2-dodecanediol | 5% | 19.5 | 17 | 20 | 17 | 16 | 13 | 44 | 50 | 40 |
| | 10% | 21 | 18 | 20.5 | 17.5 | 16.5 | 13.5 | 50 | 46 | 32 |
| Dodecanediol + Tetradecanediol | 10% + 10% | 22 | 18 | 21.5 | 17.5 | 17 | 13.5 | 50 | 46 | 40 |
| 1,2-alkanediol wherein alkane moiety has 15-18 carbon atoms | 5% | 18.5 | 16.5 | 17 | 15 | 12.5 | 10.5 | 50 | 40 | 30 | pH = 5

| | | | | | | | | | | |
|---|---|---|---|---|---|---|---|---|---|---|
| Without diol | 0 | 17.5 | 15 | 15.5 | 13 | 12 | 10 | 30 | 20 | 20 |
| 1,2-dodecane diol | 5% | 19 | 16 | 20.5 | 17.5 | 15.5 | 13 | 40 | 40 | 40 |
| 1,2-alkanediol wherein alkane moiety has 15-18 carbon atoms | 5% | 18.5 | 16 | 16.5 | 15 | 13.5 | 11 | 40 | 50 | 40 |

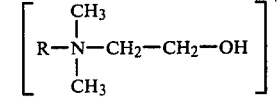
[R—N(CH₃)(CH₃)—CH₂—CH₂—OH]⁺ Cl⁻    R is alkyl derived from fatty acids of tallow pH = 3

| | | Height of foam (cm.) | | | | | | Retention of water (ml.) | | |
|---|---|---|---|---|---|---|---|---|---|---|
| | | 5% | | 2% | | 0.5% | | | | |
| 1,2-alkanediol | % | 1 | 2 | 1 | 2 | 1 | 2 | 5% | 2% | 0.5% |
| Without diol | 0 | 16 | 13.5 | 15 | 12 | 13 | 11 | 40 | 30 | 30 |
| 1,2-dodecane diol | 5% | 19.5 | 16.5 | 17.5 | 14.5 | 14.5 | 12 | 44 | 40 | 30 |

TABLE I-continued

|  | % | Height of foam (cm.) 5% | | 2% | | 0.5% | | Retention of water (ml.) 5% | 2% | 0.5% |
|---|---|---|---|---|---|---|---|---|---|---|
|  |  | 1 | 2 | 1 | 2 | 1 | 2 |  |  |  |
|  | 10% | 20.5 | 17 | 19 | 16 | 16 | 13 | 50 | 50 | 40 |
| 1,2-decane diol | 10% | 19 | 16 | 17 | 14.5 | 15 | 12 | 40 | 40 | 40 |
| 1,2-tetradecane diol | 10% | 19 |  | 16.5 |  | 14 |  | 50 | 50 | 40 |
| 1,2-alkanediol wherein alkane moiety has 15-18 carbon atoms | 5% | 16.5 | 14 | 15.5 | 13.5 | 13 | 11 | 40 | 40 | 30 |

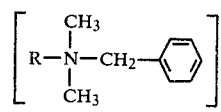 Cl⁻   sold under the tradename "Catigene T 80"
R is a mixture of dodecyl to hexadecyl pH = 7

| | | | | | | | | | | |
|---|---|---|---|---|---|---|---|---|---|---|
| Without diol | 0 | 17 | 11 | 14.5 | 8.5 | 11 | 7 | 30 | 25 | 20 |
| 1,2-dodecane diol | 5% | 18.5 | 15.5 | 17.5 | 15 | 14 | 13 | 30 | 40 | 30 |
|  | 10% | 20.5 | 17 | 18 | 15.5 | 14 | 11 | 40 | 40 | 40 |

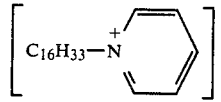 Cl⁻ pH = 7

| | | | | | | | | | | |
|---|---|---|---|---|---|---|---|---|---|---|
| Without diol | 0 | 15.5 | 12 | 15.5 | 12 | 13 | 11 | 30 | 20 | 20 |
| 1,2-alkanediol wherein alkane moiety has 11-14 carbon atoms | 10% | 20 | 15.5 | 19.5 | 16 | 16.5 | 13 | 40 | 40 | 40 |
| 1,2-alkanediol wherein alkane moiety has 15-18 carbon atoms | 10% | 17 | 14 | 16 | 13.5 | 14.5 | 12 | 50 | 40 | 40 |

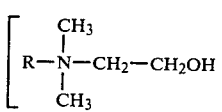 Cl⁻   R is alkyl derived from fatty acids of tallow pH = 3

| 1,2-alkanediol | % | Height of foam (cm.) 5% | | 2% | | 0.5% | | Retention of water (ml.) 5% | 2% | 0.5% |
|---|---|---|---|---|---|---|---|---|---|---|
|  |  | 1 | 2 | 1 | 2 | 1 | 2 |  |  |  |
| Without diol | 0 | 16 | 13.5 | 15 | 12 | 13 | 11 | 40 | 30 | 30 |
| Decanediol + Tetradecanediol | 5% + 5% | 20 | 17 | 19 | 15.5 | 15 | 11.5 | 40 | 50 | 40 |

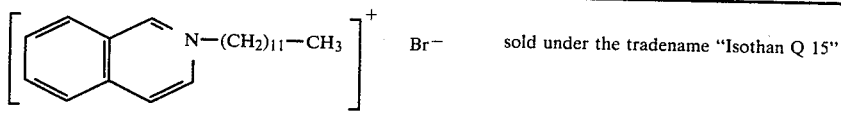 Br⁻   sold under the tradename "Isothan Q 15"

pH = 7

| | | | | | | | | | | |
|---|---|---|---|---|---|---|---|---|---|---|
| Without diol | 0 | 14 | 10 | 14 | 10 | 10 | 5 | 20 | 20 | 20 |
| 1,2-dodecanediol | 10% | 20.5 | 17 | 20 | 17 | 16 | 12 | 50 | 50 | 40 |
| Adol 158 | 10% | 17 | 14 | 16 | 13.5 | 10.5 | 8 | 40 | 40 | 20 |

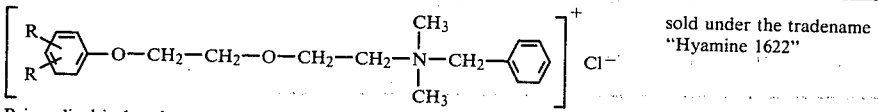 Cl⁻   sold under the tradename "Hyamine 1622"

R is radical isobutyl pH = 5.5

| | | | | | | | | | | |
|---|---|---|---|---|---|---|---|---|---|---|
| Without diol | 0 | 18.5 |  | 15 |  | 11 |  | 30 | 10 | 20 |
| 1,2-dodecanediol | 10% | 19.5 | 16.5 | 18.5 | 15 | 15 | 11 | 30 | 20 | 30 |

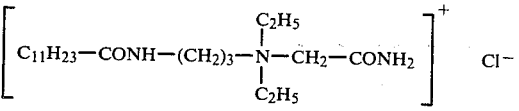 Cl⁻ pH = 3

| | | | | | | | | | | |
|---|---|---|---|---|---|---|---|---|---|---|
| Without diol | 0 | 17 | 15 | 16 | 13.5 | 13.5 | 11 | 30 | 30 | 30 |
| 1,2-dodecanediol | 5% | 20 | 17.5 | 18.5 | 16 | 16 | 12.5 | 50 | 60 | 40 |

TABLE I-continued $$\left[R-O+C_3H_6O_2\overline{\jmath_n}N\begin{matrix}CH_2-CH_2OH\\CH_2-CH_2OH\end{matrix}\right]^+ \quad SO_4CH_3$$

R is a mixture of dodecyl and tetradecyl
n = 1.5 pH = 4

| | % | 5% | | 2% | | 0.5% | | 5% | 2% | 0.5% |
|---|---|---|---|---|---|---|---|---|---|---|
| | | 1 | 2 | 1 | 2 | 1 | 2 | | | |
| Without diol | 0 | 17.5 | 15 | 15 | 12.5 | 12.5 | 10 | 30 | 40 | 30 |
| 1,2-dodecanediol | 10% | 20.5 | 18 | 20 | 17 | 16 | 13 | 50 | 50 | 30 |

$$R-COO-CH_2-CHOH-CH_2-\overset{+}{\underset{CH_3}{N}}\begin{matrix}C_2H_5\\C_2H_5\end{matrix} \quad SO_4CH_3$$

R is alkyl derived from fatty acids of coprah pH = 4

| | % | 5% | | 2% | | 0.5% | | 5% | 2% | 0.5% |
|---|---|---|---|---|---|---|---|---|---|---|
| | | 1 | 2 | 1 | 2 | 1 | 2 | | | |
| Without diol | 0 | 16 | 12.5 | 14 | 11 | 11.5 | 8.5 | 40 | 35 | 20 |
| 1,2-dodecanediol | 10% | 21 | 18.5 | 19.5 | 16.5 | 15 | 12 | 50 | 50 | 40 |

$$\left[C_{12}H_{25}-\overset{CH_3}{\underset{CH_3}{N}}-O-CH_3\right]^+ \quad SO_4CH_3^-$$

pH = 3.5

|  |  | Height of foam (cm.) | | | | | | Retention of water (ml.) | | |
|---|---|---|---|---|---|---|---|---|---|---|
| | | 5% | | 2% | | 0.5% | | | | |
| 1,2-alkanediol | % | 1 | 2 | 1 | 2 | 1 | 2 | 5% | 2% | 0.5% |
| Without diol | 0 | 14 | | 13 | | 1 | | 20 | 20 | 0 |
| Adol-114 | 10% | 18.5 | 16.5 | 20.5 | 17 | 14 | 11 | 40 | 60 | 40 |

$$\left[C_{12}H_{25}-\overset{CH_3}{\underset{CH_3}{N}}-O-CH_3\right]^+ \quad I^-$$

pH = 5

| | % | 5% | | 2% | | 0.5% | | 5% | 2% | 0.5% |
|---|---|---|---|---|---|---|---|---|---|---|
| | | 1 | 2 | 1 | 2 | 1 | 2 | | | |
| Without diol | 0 | 14.5 | 10 | 11.5 | 3 | 0.5 | | 20 | 20 | 0 |
| 1,2-alkanediol wherein alkane moiety has 11–14 carbon atoms | 10% | 17 | 13 | 17 | 15 | 11 | 8 | 20 | 30 | 30 |

$$\left[C_{12}H_{25}-O-\underset{CH_3}{N}\bigcirc\right]^+ \quad CH_3SO_3^-$$

pH = 3.5

| | % | 5% | | 2% | | 0.5% | | 5% | 2% | 0.5% |
|---|---|---|---|---|---|---|---|---|---|---|
| | | 1 | 2 | 1 | 2 | 1 | 2 | | | |
| Without diol | 0 | 12 | | 9 | | 1 | | 20 | 20 | 0 |
| 1,2-alkanediol wherein alkane moiety has 11–14 carbon atoms | 10% | 17.5 | 14.5 | 18 | 15 | 12 | 8 | 40 | 50 | 30 |

$$\left[C_{12}H_{25}-\overset{+}{\underset{CH_3}{S}}-CH_2-CH_2OH\right]^+ \quad SO_4CH_3^-$$

pH = 2.5

|  |  | Height of foam (cm.) | | | | | | Retention of water (ml.) | | |
|---|---|---|---|---|---|---|---|---|---|---|
| | | 5% | | 2% | | 0.5% | | | | |
| 1,2-alkanediol | % | 1 | 2 | 1 | 2 | 1 | 2 | 5% | 2% | 0.5% |
| Without diol | 0 | 15.5 | 5 | 10 | 7 | 6 | 3 | 20 | 10 | 10 |
| 1,2-dodecane diol | 10% | 19.5 | 17 | 18.5 | 15 | 9 | 6 | 40 | 50 | 20 |

$$\left[C_{12}H_{25}-\overset{+}{\underset{CH_3}{S}}-CH_2-CHOH-CH_2-\overset{+}{\underset{CH_3}{N}}\begin{matrix}C_2H_5\\C_2H_5\end{matrix}\right] \quad 2\,SO_4CH_3^-$$

pH = 4

| | % | 5% | | 2% | | 0.5% | | | | |
|---|---|---|---|---|---|---|---|---|---|---|
| Without diol | 0 | 2 | 0 | 2 | 0 | 2 | 0 | | | |
| 1,2-alkanediol wherein alkane moiety has 11–14 | | | | | | | | | | |

TABLE I-continued

| carbon atoms | 10% | 19 | 15.5 | 14.5 | 11 | 12.5 | 5.5 | 40 | 40 | 20 |

$$R-\underset{\underset{CH_3}{|}}{\overset{\overset{CH_3}{|}}{N}}-CH_2-COO^-$$

sold under the tradename "EMPIGEN BN"
R is a mixture of dedecyl and tetradecyl pH = 4.5

| | | | | | | | | | | |
|---|---|---|---|---|---|---|---|---|---|---|
| Without diol | 0 | 18 | 16.5 | 16.5 | 14.5 | 16 | 13 | 30 | 20 | 30 |
| 1,2-dodecanediol | 10% | 22.5 | 19.5 | 19 | 16.5 | 18.5 | 15.5 | 50 | 30 | 50 |

$$R-CONH-(CH_2)_3-\underset{\underset{CH_2-COO^-}{|}}{\overset{+}{N}}\begin{matrix}CH_3\\CH_3\end{matrix}$$

sold under the tradename "Tego Betaine L7"
R is lauryl pH = 4

| | | | | | | | | | | |
|---|---|---|---|---|---|---|---|---|---|---|
| Without diol | 0 | 17 | 14 | 15 | 13.5 | 13.5 | 10.5 | 30 | 30 | 30 |
| 1,2-alkanediol wherein alkane moiety has 11–14 carbon atoms | 10% | 20 | 17 | 19.5 | 16 | 17 | 14 | 40 | 40 | 40 |

$$R-N\begin{matrix}CH_2-CH_2-COONa\\CH_2-CH_2-COONa\end{matrix}$$

sold under the tradename "Deriphat 160"
R is lauryl pH = 9

| | | Height of foam (cm.) | | | | | | Retention of water (ml.) | | |
|---|---|---|---|---|---|---|---|---|---|---|
| | | 5% | | 2% | | 0.5% | | | | |
| 1,2-alkanediol | % | 1 | 2 | 1 | 2 | 1 | 2 | 5% | 2% | 0.5% |
| Without diol | 0 | 18.5 | 15 | 16.5 | 13 | 10.5 | 7 | 40 | 40 | 20 |
| 1,2-dodecane diol | 10% | 23 | 20 | 20 | 17 | 17.5 | 14.5 | 70 | 60 | 40 |
| 1,2-alkanediol wherein the alkane moiety has 11–14 carbon atoms | 10% | 21.5 | 17.5 | 20 | 17 | 14.5 | 12 | 60 | 50 | 40 |

$$C_{11}H_{23}-\underset{\underset{OH}{|}}{\overset{\overset{N}{\|}}{C}}\begin{matrix}CH_2\\ \\ \end{matrix}\begin{matrix}CH_2\\N\\CH_2-COONa\end{matrix}CH_2-CH_2-O-CH_2-COONa$$

sold under the tradename "Miranol C2M"

pH = 8

| | | | | | | | | | | |
|---|---|---|---|---|---|---|---|---|---|---|
| Without diol | 0 | 18.5 | 16.5 | 18 | 15.5 | 14.5 | 11.5 | 40 | 40 | 40 |
| 1,2-dodecane diol | 10% | 23 | 19.5 | 20 | 17 | 17 | 14.5 | 60 | 50 | 40 |

$$CH_3-\overset{+}{N}\begin{matrix}\diagup\diagdown\\O\\\diagdown\diagup\end{matrix}\quad Cl^-$$
$$CH_2-CONH-(CH_2)_3-\underset{\underset{R}{|}}{N}-CH_2-COONa$$

R is alkyl derived from fatty acids of coprah pH = 8

| | | | | | | | | | | |
|---|---|---|---|---|---|---|---|---|---|---|
| Without diol | 0 | 14 | | 12.5 | | 9 | | 30 | 30 | 20 |
| 1,2-alkanediol wherein alkane moiety has 11–14 carbon atoms | 10% | 19.5 | 16.5 | 16.5 | 13.5 | 12.5 | 10 | 50 | 40 | 40 |

$$R-\underset{\underset{CH-COOH}{|}}{NH}\quad CH_2-CONH-(CH_2)_3-N\begin{matrix}C_2H_5\\C_2H_5\end{matrix}$$

R is hydrocarbon chain derived from fatty acids of coprah     pH = 8

| | | Height of foam (cm.) | | | | | | Retention of water (ml.) | | |
|---|---|---|---|---|---|---|---|---|---|---|
| | | 5% | | 2% | | 0.5% | | | | |
| 1,2-alkanediol | % | 1 | 2 | 1 | 2 | 1 | 2 | 5% | 2% | 0.5% |
| Without diol | 0 | 19 | 17 | 17.5 | 14.5 | 13 | 11 | 40 | 40 | 30 |
| 1,2-dodecanediol | 5% | 21.5 | 18.5 | 19.5 | 16.5 | 15.5 | 11.5 | 50 | 50 | 40 | pH = 3.5

| | | | | | | | | | | |
|---|---|---|---|---|---|---|---|---|---|---|
| Without diol | 0 | 19.5 | 17 | 18 | 15 | 13.5 | 11 | 40 | 40 | 30 |
| 1,2-dodecanediol | 5% | 23 | 19.5 | 20.5 | 18 | 16 | 13 | 60 | 50 | 40 |
| | 10% | 23 | 18.5 | 21 | 18 | 17 | 14 | 60 | 60 | 50 |
| 1,2-tetradecane diol | 10% | 23 | 20 | 21 | 18 | 16 | 13.5 | 70 | 70 | 50 |
| 1,3-decanediol | 10% | 21 | 18 | 20.5 | 17 | 15.5 | 13 | 50 | 50 | 40 |
| 1,2-decanediol + 1,2-tetradecane diol | 5% + 5% | 21.5 | 18 | 20.5 | 17.5 | 15.5 | 13 | 50 | 60 | 40 |

The following non-limiting Examples are given to illustrate the invention. Unless otherwise stated, all parts and percentages are by weight.

EXAMPLES OF USE

A. Shampoo Compositions

Example 1

The following composition is prepared:
Trimethyl tetradecyl ammonium bromide of the formula

| $\left[\begin{array}{c} CH_3 \\ | \\ C_{14}H_{29}-N-CH_3 \\ | \\ CH_3 \end{array}\right]^+ Br^-$ | 6 g |
|---|---|
| $C_{12}H_{25}-CHOH-CH_2OH$ | 0.6 g |
| Lactic acid, q.s.p. | pH 4 |
| Water, q.s.p. | 100 g |

A clear composition is obtained which is definitely more foamy and somewhat more effective as a detergent than a solution of trimethyl tetradecyl ammonium bromide at the same concentration. When applied as a shampoo, this composition yields a consistent, stable foam.

Example 2

The following composition is prepared:

| $\left[\begin{array}{c} CH_3 \\ | \\ C_{14}H_{29}-N-CH_3 \\ | \\ CH_3 \end{array}\right]^+ Br^-$ | 5 g |
|---|---|
| $R-CHOH-CH_2O-[CH_2-CHOH-CH_2O]_3-H$, wherein R is a mixture of nonyl to dodecyl | 5 g |
| $C_{12}H_{25}-CHOH-CH_2OH$ | 1 g |
| Lactic acid, q.s.p. | pH 3 |
| Water, q.s.p. | 100 g |

The volume and stability of the foam of this shampoo is clearly greater than that of the corresponding cationic solution.

Example 3

The following composition is prepared:

| $\left[\begin{array}{c} CH_3 \\ | \\ R-N-CH_2-CH_2OH \\ | \\ CH_3 \end{array}\right]^+ Cl^-$, wherein R is alkyl derived from fatty acids of tallow | 5 g |
|---|---|
| $C_{12}H_{25}-O-CH_2-CHOH-CH_2OH$ | 0.5 g |
| Lactic acid, q.s.p. | pH 4 |
| Water, q.s.p. | 100 g |

The volume and stability of the foam of this shampoo is clearly greater than that of the corresponding cationic solution.

Example 4

The following composition is prepared:

| $\left[\begin{array}{c} CH_3 \\ | \\ R-N-CH_2-CH_2OH \\ | \\ CH_3 \end{array}\right]^+ Cl^-$ wherein R is alkyl derived from fatty acids of tallow | 3 g |
|---|---|
| Lauryl alcohol oxyethylenated with 12 moles ethylene oxide | 7 g |
| $C_{10}H_{21}-CHOH-CH_2OH$ | 0.9 g |
| Lactic acid, q.s.p. | pH 3 |
| Water, q.s.p. | 100 g |

A very foamy shampoo with excellent initiation of foaming is thus produced.

Example 5

The following composition is prepared:

| $R-NH-CH-COOH$ <br> $\quad\quad |$ <br> $\quad\quad CH_2-CONH-(CH_2)_3-N{<}^{C_2H_5}_{C_2H_5}$ <br> wherein R is alkyl derived from the fatty acids of copra | 10 g |
|---|---|
| $C_{10}H_{21}-CHOH-CH_2OH$ | 1 g |
| Lactic acid, q.s.p. | pH 5 |
| Water, q.s.p. | 100 g |

The volume and stability of the foam of this shampoo is clearly greater than is the volume and stability of the foam in the corresponding cationic solution.

When adjusted to pH 8.5, using triethanolamine, the foam is similar to that obtained at pH 5.

Example 6

The following composition is prepared:

| $R-NH-CH-COOH$ <br> $\quad\quad |$ <br> $\quad\quad CH_2-CONH-(CH_2)_3-N{<}^{C_2H_5}_{C_2H_5}$ <br> wherein R is alkyl derived from fatty acids of copra | 4 g |
|---|---|
| $R-N{\overset{CH_3}{\underset{CH_3}{|}}}{\to}O$, wherein R is lauryl | 5 g |
| $C_{12}H_{25}-O+C_2H_3O(CH_2OH)\overline{)_{3.2}}H$ | 5 g |
| $C_{12}H_{25}-CHOH-CH_2OH$ | 2.5 g |
| Lactic acid, q.s.p. | pH 4 |
| Water, q.s.p. | 100 g |

The volume and stability of the foam of this shampoo is clearly greater than that obtained in the corresponding cationic solution.

Example 7

The following composition is prepared:

| | |
|---|---|
| $C_{11}H_{23}-C\underset{\overset{\parallel}{OH}}{\overset{N\diagdown CH_2\diagup CH_2}{\diagdown}}N\diagup{CH_2-CH_2-O-CH_2-COONa}\diagdown{CH_2-COONa}$ | 17.5 g |
| $C_{12}H_{25}-CHOH-CH_2OH$ | 2 g |
| Triethanolamine, q.s.p. | pH 8 |
| Water, q.s.p. | 100 g |

The volume and stability of the foam of this shampoo is clearly greater than that of the corresponding cationic solution.

Example 8

The following composition is prepared:

| | |
|---|---|
| $R-N\diagup{CH_2-CH_2-COONa}\diagdown{CH_2-CH_2-COONa}$, wherein R is lauryl | 15 g |
| $C_{10}H_{21}-CHOH-CH_2OH$ | 1.5 g |
| Triethanolamine, q.s.p. | pH 8.5 |
| Water, q.s.p. | 100 g |

This shampoo composition is definetely more foamy and detergent than one prepared without the above dodecane diol. Further, the foam of the composition made in accordance with the present invention is also more creamy and more stable.

Example 9

The following dye shampoo is prepared:

| | |
|---|---|
| Sodium N-lauryl-β-iminodipropionate, sold under the tradename "Deriphate 160" | 15 g |
| 1,2-dodecanediol | 1.5 g |
| 1-methylamino 2-nitro (2'-hydroxyethyl)-4-methylaminobenzene | 0.66 g |
| 1,3-diamino 4-nitro benzene | 0.07 g |
| Violet acetoquinone LUMIERE N, (C.F.M.C.), CI acid violet 4 (61105) p. 1706 of the Colour Index 2nd ed., 1956 | 0.30 g |
| Diazo black, Cibacete GWS (CIBA) CI disperse black 22, p. 224 of the Color Colour supplement 1963 | 0.80 g |
| Red acetoquinone LUMIERE BZ (C.F.M.C.) CI disperse red 17, (11210) p. 1695 of the Colour Index 2nd ed, 1956 | 0.45 g |
| Dark blue acetoquinone 5 R, (C.F.M.C.) CI disperse blue 2, p. 1713 of the Colour Index 2nd ed, 1956 | 0.40 g |
| Yellow acetoquinone LUMIERE 4JLZ (C.F.M.C.) CI disperse yellow 3 (11855) p. 1660 of the Colour Index 2nd ed, 1956 | 0.05 g |
| Violet, Cibacete RB (CIBA) CI disperse violet 15, p. 1711 of the Colour Index 2nd ed, 1956 | 0.40 g |
| Butoxy-2-ethanol (butyl cellosolve) | 3 g |
| 20% solution citric acid, q.s.p. | pH 9.5 |
| Water, q.s.p. | 100 g |

This shampoo is applied to chestnut hair with 60% white hair. From the start of the shampoo there is abundant foam.

In a second shampoo stage, the product is allowed to stand 20 minutes to obtain the dye effect. Thereafter, the hair is rinsed and a dark chestnut hue is obtained that adequately masks the original white hair.

Example 10

The following dye shampoo is prepared:

| | |
|---|---|
| Cetyl trimethylammonium chloride | 3 g |
| Lauryl alcohol oxyethylenated with 12 moles ethylene oxide | 7 g |
| 1,2 dodecane diol | 0.7 g |
| Violet, Cebacete RB (CIBA), CI disperse violet 15, p. 1711 of the Colour Index 2nd ed, 1956 | 0.30 g |
| Violet, Vialon solid RRL, (B.A.S.F.) CI disperse violet 99, page 63 of the Colour Index suppl. 1963 | 0.24 g |
| 20% solution citric acid, q.s.p. | pH 5 |
| Water, q.s.p. | 100 g |

This dye shampoo is applied as a conventional two-stage shampoo, on 100% white hair. In the first stage there is obtained a smooth, abundant foam and in the second stage, the foam is allowed to stand on the hair for 5 minutes. There is thus imparted to the hair a pearly grey light sheen.

Example 11

The following dye shampoo is prepared:

| | |
|---|---|
| $R-NH-CH-COONa\underset{CH_2-CONH(CH_2)_3-N\diagup{C_2H_5}\diagdown{C_2H_5}}{|}$, wherein R is alkyl derived from fatty acids of copra | 6.0 g |
| Lauryl alcohol oxyethylenated with 12 moles ethylene oxide | 15.0 g |
| Diethanolamide of copra | 3.5 g |
| 1,2-dodecanediol | 1.5 g |
| Ammonia, 22° Be | 10 ml |
| DYES: | |
| 2,4-diaminoanisole sulfate | 0.050 g |
| Resorcinol | 0.490 g |
| m-aminophenol base | 0.200 g |
| p-aminophenol base | 0.210 g |
| p-toluylenediamine | 1.250 g |
| Thioglycol acid | 0.250 g |
| Ethylenediamine tetraacetic acid | 2.0 g |
| Water, q.s.p. | 100 g |

Fifty grams of this dye shampoo are mixed with the same amount of hydrogen peroxide (20 volumes), and the resulting mixture is applied to brown hair with an applicator or brush. The hair is shampooed until foam, which is abundant, is obtained. Thereafter, the shampoo is permitted to remain in contact with the hair for 30 minutes, after which the hair is rinsed and dried. There is thus imparted to the hair a chestnut hue.

Example 12

The following shampoo composition is prepared:

| | |
|---|---|
| $R-N-CH_2-CH_2-COONa\underset{CH_2-CH_2-COONa}{|}$, wherein R is alkyl having 12-14 carbon atoms | 25 g |
| $C_8H_{17}-CHOH-CH_2OH$ | 4 g |
| Perfume | 0.5 g |
| Triethanolamine q.s.p. | pH 8 |
| Water q.s.p. | 100 g |

The volume and stability of the foam of this shampoo is clearly greater than that of corresponding amphoteric solution.

B. Bubble Bath Compositions

Example 13

The following bubble bath formulation is prepared:

| | |
|---|---|
| R—NH—CH—COOH<br>            \|<br>           CH$_2$—CONH—(CH$_2$)$_3$—N(C$_2$H$_5$)$_2$ wherein R is a hydrocarbon radical derived from fatty acids of copra | 10 g |
| C$_{11}$H$_{23}$—C(=N—CH$_2$—CH$_2$)—N(—CH$_2$—CH$_2$—O—CH$_2$COONa)(CH$_2$COONa) with OH | 30 g |
| Lauryl alcohol oxyethylenated with 12 moles ethylene oxide | 5 g |
| C$_{10}$H$_{21}$—CHOH—CH$_2$OH | 3 g |
| Lactic acid, q.s.p. | pH 6 |
| Perfume | 3 g |
| Water, q.s.p. | 100 g |

A concentrated, viscous foaming composition results which exhibits excellent foaming capability.

Example 14

The following bubble bath formulation is prepared:

| | |
|---|---|
| C$_{11}$H$_{23}$—C(=N—CH$_2$—CH$_2$)—N(—CH$_2$—CH$_2$—O—CH$_2$COONa)(CH$_2$COONa) with OH | 60 g |
| Lauryl alcohol oxyethylenated with 12 moles ethylene oxide | 12 g |
| C$_{10}$H$_{21}$—CHOH—CH$_2$OH | 5 g |
| Lactic acid, q.s.p. | pH 6.5 |
| Perfume | 5 g |
| Water, q.s.p. | 100 g |

A concentrated foaming composition with excellent initiation of foaming and high foam yield is thus produced.

Although not always actually stated, the compositions in these Examples generally contain a sufficient quantity of a perfume to add to the aesthetic appeal of the composition.

What is claimed is:

1. A shampoo composition consisting essentially of an aqueous solution of
   (a) 0.5–30 percent by weight based on the total weight of the composition of a surfactant selected from the group consisting of

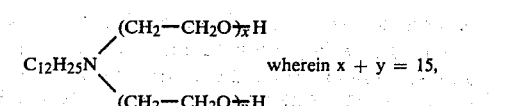

(1)

wherein x + y = 15,

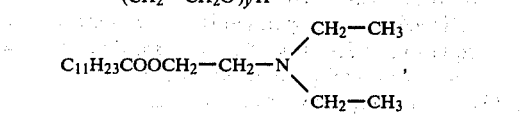

(2)

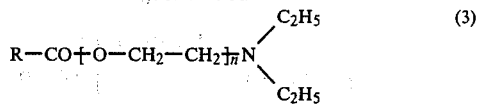

(3)

wherein R is the hydrocarbon chain from the fatty acids of copra and n=2.5,

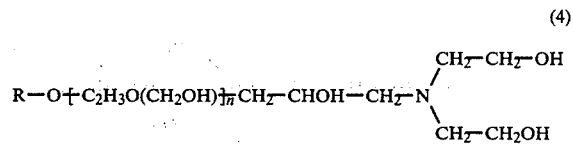

(4)

wherein R is the hydrocarbon radical of oleic acid and n=1,

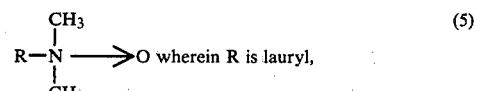

(5)

wherein R is lauryl,

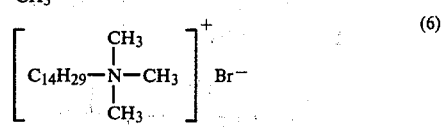

(6)

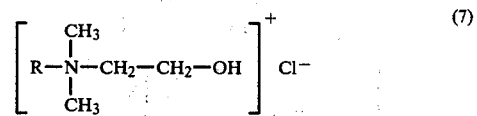

(7)

wherein R is the alkyl from the fatty acids of tallow,

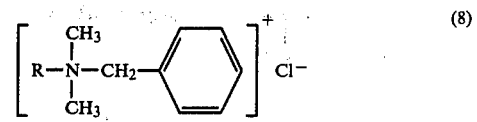

(8)

wherein R is a mixture of dodecyl to hexadecyl,

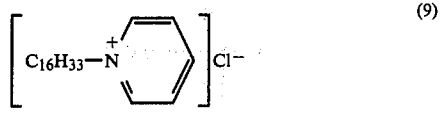

(9)

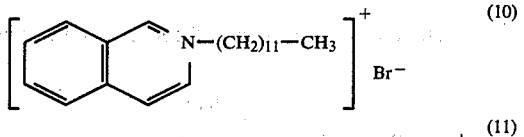

(10)

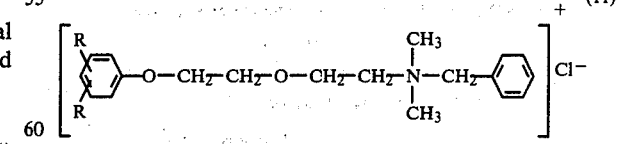

(11)

wherein R is isobutyl,

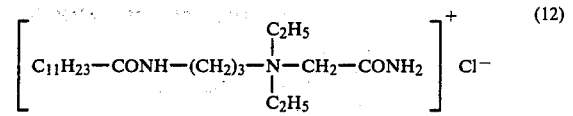

(12)

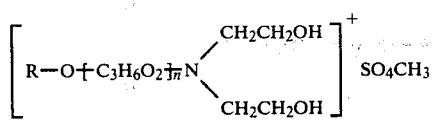 (13)

wherein R is a mixture of doecyl and tetradecyl, and n=1.5,

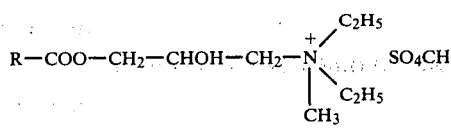 (14)

wherein R is the alkyl from the fatty acids of copra,

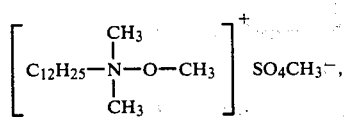 (15)

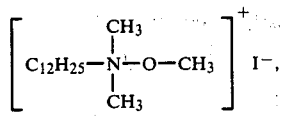 (16)

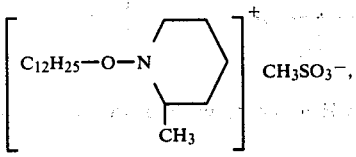 (17)

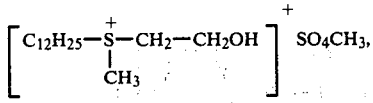 (18)

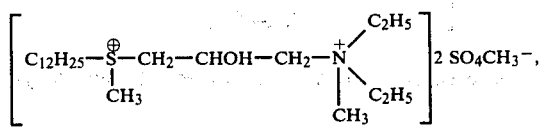 (19)

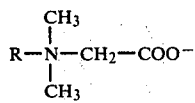 (20)

wherein R is a mixture of dodecyl and tetradecyl,

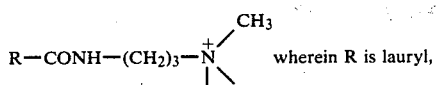 (21) wherein R is lauryl,

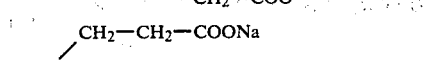 (22) wherein R is lauryl,

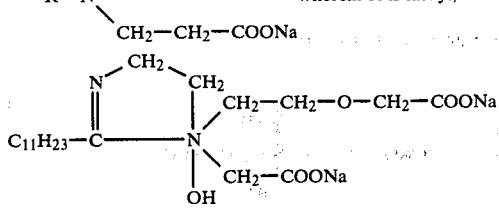 (23)

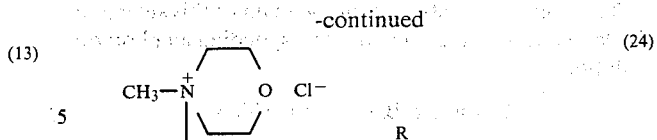 (24)

wherein R is the alkyl of the fatty acids of copra and

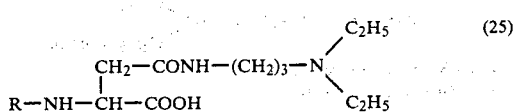 (25)

wherein R is the hydrocarbon chain from the fatty acids of copra and mixtures thereof; and (b) 0.4 to 4.5 percent by weight based on the total weight of the composition of a straight chain 1,2-alkane diol selected from the group consisting of 1,2-alkane diols having 10–14 carbon atoms, and mixtures thereof.

2. The shampoo composition of claim 1 which also includes a nonionic surfactant in an amount such that the resulting composition exhibits improved foam characteristics.

3. The shampoo composition of claim 1 which also includes
0.5–30 percent by weight based on the total weight of the composition of a nonionic surfactant selected from the group consisting of
(1) the condensation product of ethylene oxide with
  (i) a fatty alcohol, (ii) a long chain mercaptan or
  (iii) an alkyl phenol,
(2) a compound having the formula RO—[C$_2$H$_3$O(CH$_2$OH)]$_n$—H wherein R represents alkyl having 8–22 carbon atoms, alkenyl having 8–22 carbon atoms, alkyl aryl having 8–22 carbon atoms wherein the alkyl moiety has 2–16 carbon atoms, a hydrocarbon radical derived from an alcohol obtained by the hydrogenation of lanolin or a hydrocarbon radical derived from a natural wax, a resin acid or a cyclic fatty acid, and n is a whole or decimal number equal to or lower than 10,
(3) a compound having the formula RO—[C$_2$H$_3$O(CH$_2$OCH$_2$—CHOH—CH$_2$OH)]$_n$—H wherein R represents alkyl having 8–22 carbon atoms, alkenyl having 8–22 carbon atoms, alkyl having 8–22 carbon atoms and substituted by hydroxy or a heteroatom, alkenyl having 8–22 carbon atoms and substituted by hydroxy or a heteroatom, an n is a whole or decimal number equal to or lower than 5,
(4) a compound of the formula

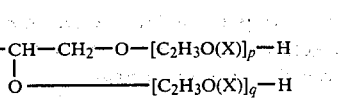

wherein R is a hydrocarbon having 8–22 carbon atoms or a hydrocarbon having 8–22 carbon atoms and substituted by hydroxy or a heteroatom, X represents CH$_2$OH or CH$_2$OCH$_2$—CHOH—CH$_2$OH, each of p and q is a whole or decimal number equal to or less than 10, the sum of (p+q) being equal to or greater than 1 and lower or equal to 10,
(5) a compound having the formula $$R-S-[CH_2-CHOH-CH_2-O]_n-H$$
$$\downarrow$$
$$O$$

wherein R represents alkyl having 8-22 carbon atoms, alkenyl having 8-22 carbon atoms, hydroxy alkyl wherein the alkyl moiety has 8-22 carbon atoms, cycloaliphatic radical having 8-22 carbon atoms, arylaliphatic radical having 8-22 carbon atoms or a mixture thereof, and n is a whole or decimal number greater than 1 and equal to or less than 10, (6) a compound of the formula $$R-CHOH-CH_2-O-[CH_2-CHOH-CH_2]_n-H$$

wherein R represents aliphatic, cycloaliphatic or arylaliphatic, or mixtures thereof, each having 7-21 carbon atoms and wherein the aliphatic moiety of each is unsubstituted or substituted with oxygen or sulfur and n represents a whole or decimal number greater than 1 and equal to or lower than 10, and (7) a compound of the formula $$RO-\left[\begin{array}{cc}CH-CHO\\|\quad\;\;|\\A\quad B\end{array}\right]_n-H$$

wherein R represents alkyl having 8-30 carbon atoms, alkylaryl having 12-40 carbon atoms, alkylpolyalkyleneoxy containing 14-60 carbon atoms and 1-10 oxygen atoms or cycloaliphatic radical having 10-30 carbon atoms, one of A and B represents hydrogen and the other represents CH$_2$Z wherein Z represents R'S- or $$R'S-$$
$$\|$$
$$O$$

wherein R' is alkyl or hydroxyalkyl having 1-4 carbon atoms and n is whole number between 1-20, inclusive.

4. The shampoo composition of claim 1 which also includes a perfume.

5. A bubble bath composition consisting essentially of an aqueous solution of (a) 10-80 percent by weight based on the total weight of the composition of a surfactant selected from the group consisting of (1)
$$C_{12}H_{25}N\begin{array}{c}(CH_2-CH_2O)_xH\\ \\(CH_2-CH_2O)_yH\end{array}\quad\text{wherein } x+y=15,$$

(2)
$$C_{11}H_{23}COOCH_2-CH_2-N\begin{array}{c}CH_2-CH_3\\ \\CH_2-CH_3\end{array}$$

(3)
$$R-CO+O-CH_2-CH_2\!)_{\overline{n}}N\begin{array}{c}C_2H_5\\ \\C_2H_5\end{array}$$

wherein R is the hydrocarbon chain from the fatty acids of copra and n=2.5, (4)
$$R-O+C_2H_3O(CH_2OH)\!)_{\overline{n}}CH_2-CHOH-CH_2-N\begin{array}{c}CH_2-CH_2-OH\\ \\CH_2-CH_2OH\end{array}$$

wherein R is the hydrocarbon radical of oleic and acid and n=1, (5)
$$R-\underset{\underset{CH_3}{|}}{\overset{\overset{CH_3}{|}}{N}}\longrightarrow O\quad\text{wherein R is lauryl,}$$

(6)
$$\left[C_{14}H_{29}-\underset{\underset{CH_3}{|}}{\overset{\overset{CH_3}{|}}{N}}-CH_3\right]^+\;Br^-$$

(7)
$$\left[R-\underset{\underset{CH_3}{|}}{\overset{\overset{CH_3}{|}}{N}}-CH_2-CH_2-OH\right]^+\;Cl^-$$

wherein R is the alkyl from the fatty acids of tallow, (8)
$$\left[R-\underset{\underset{CH_3}{|}}{\overset{\overset{CH_3}{|}}{N}}-CH_2-\text{Ph}\right]^+\;Cl^-$$

wherein R is a mixture of dodecyl to hexadecyl, (9)
$$\left[C_{16}H_{33}-N^+\text{Pyr}\right]\;Cl^-$$

(10)
$$\left[\text{Naphth}-N-(CH_2)_{11}-CH_3\right]^+\;Br^-$$

(11)
$$\left[\text{R}_2\text{Ph}-O-CH_2-CH_2-O-CH_2-CH_2-\underset{\underset{CH_3}{|}}{\overset{\overset{CH_3}{|}}{N}}-CH_2-\text{Ph}\right]^+\;Cl^-$$

wherein R is isobutyl,

(12)
$$\left[C_{11}H_{23}-CONH-(CH_2)_3-\underset{\underset{C_2H_5}{|}}{\overset{\overset{C_2H_5}{|}}{N}}-CH_2-CONH_2\right]^+\;Cl^-$$

(13)
$$\left[R-O+C_3H_6O_2\!)_{\overline{n}}N\begin{array}{c}CH_2CH_2OH\\ \\CH_2CH_2OH\end{array}\right]^+\;SO_4CH_3$$

wherein R is a mixture of doecyl and tetradecyl, and n=1.5,

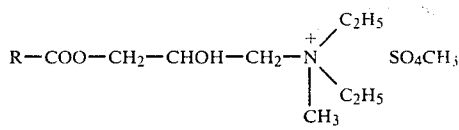 (14)

wherein R is the alkyl from the fatty acids of copra,

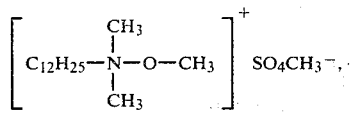 (15)

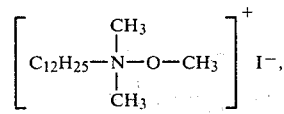 (16)

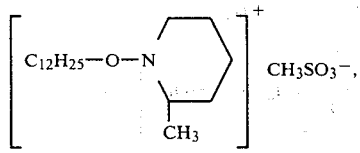 (17)

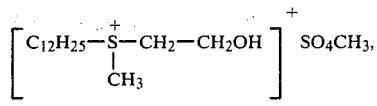 (18)

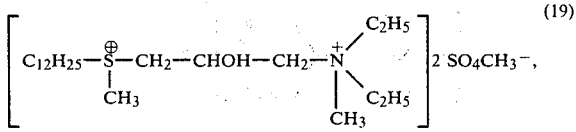 (19)

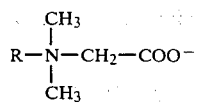 (20)

wherein R is a mixture of dodecyl and tetradecyl,

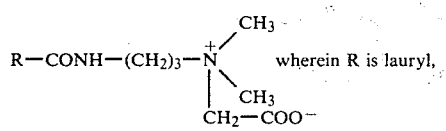 (21)

wherein R is lauryl,

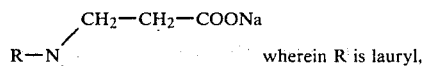 (22)

wherein R is lauryl,

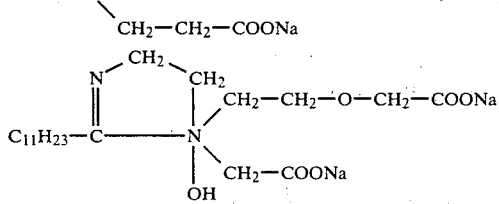 (23)

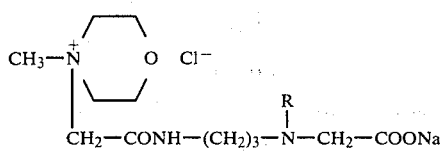 (24)

wherein R is the alkyl of the fatty acids of copra and

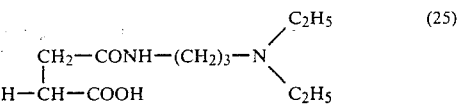 (25)

wherein R is the hydrocarbon chain from the fatty acids of copra and mixtures thereof; and (b) 1–10 percent by weight based on the total weight of the composition of a straight chain 1,2-alkane diol selected from the group consisting of 1,2-alkane diols having 10–14 carbon atoms, and mixtures thereof.

6. The bubble bath composition of claim 5 which also includes a nonionic surfactant in an amount such that the resulting composition exhibits improved foam characteristics.

7. The bubble bath composition of claim 5 which also includes 10–80 percent by weight based on the total weight of the composition of a nonionic surfactant selected from the group consisting of (1) the condensation product of ethylene oxide with (i) a fatty alcohol, (ii) a long chain mercaptan or (iii) an alkyl phenol, (2) a compound having the formula RO—[$C_2H_3O(CH_2OH)$]$_n$—H wherein R represents alkyl having 8–22 carbon atoms, alkenyl having 8–22 carbon atoms, alkylaryl having 8–22 carbon atoms wherein the alkyl moiety has 2–16 carbon atoms, a hydrocarbon radical derived from an alcohol obtained by the hydrogenation of lanolin or a hydrocarbon radical derived from a natural wax, a resin acid or a cyclic fatty acid, and n is a whole or decimal number equal to or lower than 10, (3) a compound having the formula RO—[$C_2H_3O(CH_2OCH_2$—CHOH—$CH_2OH)$]$_n$—H wherein R represents alkyl having 8–22 carbon atoms, alkenyl having 8–22 carbon atoms, alkyl having 8–22 carbon atoms and substituted by hydroxy or a heteroatom, alkenyl having 8–22 carbon atoms and substituted by hydroxy or a heteroatom, and n is a whole or decimal number equal to or lower than 5, (4) a compound of the formula

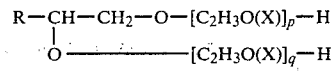

wherein R is a hydrocarbon having 8–22 carbon atoms or a hydrocarbon having 8–22 carbon atoms and substituted by hydroxy or a heteroatom, X represents $CH_2OH$ or $CH_2OCH_2$—CHOH—$CH_2OH$, each of p and q is a whole or decimal number equal to or less than 10, the sum of (p+q) being equal to or greater than 1 and lower or equal to 10, (5) a compound having the formula

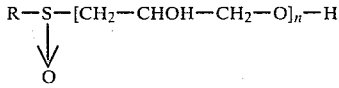

wherein R represents alkyl having 8–22 carbon atoms, alkenyl having 8–22 carbon atoms, hydroxy alkyl wherein the alkyl moiety has 8–22 carbon atoms, cycloaliphatic radical having 8–22 carbon atoms, arylaliphatic radical having 8–22 carbon atoms or a mixture thereof, and n is a whole or decimal number greater than 1 and equal to or less than 10, (6) a compound of the formula R—CHOH—CH$_2$—O—[CH$_2$—CHOH—CH$_2$]$_n$—H wherein R represents aliphatic, cycloaliphatic or arylaliphatic, or mixtures thereof, each having 7-21 carbon atoms and wherein the aliphatic moiety of each is unsubstituted or substituted with oxygen or sulfur and n represents a whole or decimal number greater than 1 and equal to or lower than 10, and (7) a compound of the formula

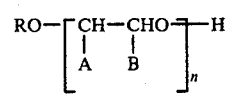

wherein R represents alkyl having 8-30 carbon atoms, alkylaryl having 12-40 carbon atoms, alkylpolyalkyleneoxy containing 14-60 carbon atoms and 1-10 oxygen atoms or cycloaliphatic radical having 10-30 carbon atoms, one of A and B represents hydrogen and the other represents CH$_2$Z wherein Z represents R'S- or

wherein R' is alkyl or hydroxyalkyl having 1-4 carbon atoms and n is a whole number between 1-20, inclusive.

8. The bubble bath composition of claim 5 which also includes a perfume.

* * * * *